US00PP32102P2

(12) United States Plant Patent
Fitzgerald

(10) Patent No.: US PP32,102 P2
(45) Date of Patent: Aug. 18, 2020

(54) ***CORDYLINE* PLANT NAMED 'FILIRESTA'**

(50) Latin Name: *Cordyline australis*
Varietal Denomination: FILIRESTA

(71) Applicant: Beotanics Ltd., Stoneyford (IE)

(72) Inventor: Pat Fitzgerald, Stoneyford (IE)

(73) Assignee: BEOTANICS LTD., Stoneyford (IE)

( * ) Notice: Subject to any disclaimer, the term of this patent is extended or adjusted under 35 U.S.C. 154(b) by 0 days.

(21) Appl. No.: 16/602,441

(22) Filed: Oct. 4, 2019

(30) Foreign Application Priority Data

May 28, 2019 (QZ) ..... PBR 2019/1324

(51) Int. Cl.
*A01H 5/00* (2018.01)
*A01H 6/12* (2018.01)

(52) U.S. Cl.
USPC ..... Plt./383

(58) Field of Classification Search
USPC ..... Plt./383
CPC ..... A01H 5/00; A01H 6/12
See application file for complete search history.

*Primary Examiner* — Annette H Para
(74) *Attorney, Agent, or Firm* — Penny J. Aguirre

(57) ABSTRACT

A new cultivar of *Cordyline australis* plant named 'FILIRESTA' that is characterized by its compact and sturdy plant habit, its foliage that is dark brown-purple in color and narrow in width, its plant habit that is stable, drought and heat resistant with no observed diseases, and its good performance in a container.

2 Drawing Sheets

Botanical classification: *Cordyline australis.*
Cultivar designation: 'FILIRESTA'.

CROSS-REFERENCE TO A RELATED APPLICATION

This application claims priority to European Community Plant Variety Office (CPVO) Plant Breeder's Rights Application No. 2019/1324 filed on May 28, 2019, the entire contents of which is incorporated by reference herein.

BACKGROUND OF THE INVENTION

The present invention relates to a new and distinct cultivar of *Cordyline australis* and will be referred to hereafter by its cultivar name, 'FILIRESTA'. 'FILIRESTA' represents a new cultivar of cabbage tree or cabbage palm and is grown as a foliage plant for landscape and container use.

The new cultivar was discovered as a naturally-occuring chimeral mutation by the Inventor in Old Town, Stoneyford, Ireland in autumn of 2017 of *Cordyline australis* 'Red Star' (not patented) that was growing in a container.

Asexual propagation of the new cultivar was first accomplished by tissue culture using meristemac tissue by the Inventor in Old Town, Stoneyford, Ireland in autumn of 2017. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'FILIRESTA' as a new and unique cultivar of *Cordyline.*

1. 'FILIRESTA' exhibits a compact and strong plant habit.
2. 'FILIRESTA' exhibits foliage that is dark brown-purple in color.
3. 'FILIRESTA' exhibits a plant habit that stable, drought and heat resistant with no observed diseases.
4. 'FILIRESTA' exhibits good performance in a container.
5. 'FILIRESTA' exhibits foliage that is fine (narrow).

The parent plant of 'FILIRESTA', 'Red Star' differs from 'FILIRESTA' in having leaves that are lighter in color and wider and in having a less compact plant habit with a taller and wider plant size. 'FILIRESTA' can be compared to the *Corydyline* cultivars 'Norfire' (U.S. Plant Pat. No. 21,220) and 'Charlie Boy' (U.S. Plant Pat. No. 20,137). 'Norfire' is similar to 'FILIRESTA' in having narrow dark foliage with a very narrow margin. 'Norfire' differs from 'FILIRESTA' in having foliage that is more purple in color and a wider plant habit. 'Charlie Boy' is similar to 'FILIRESTA' in having brown-purple foliage. 'Charlie Boy' differs from 'FILIRESTA' in having distinct margins that are pink in color (variegaed) and in having a less compact plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but is not limited to a website listing by Sycamore Trading Company.

BRIEF DESCRIPTION OF THE DRAWINGS

The accompanying colored photographs illustrate the overall appearance and distinct characteristics of the new

*Cordyline*. The photographs were taken of a 1.5-year-old plant of 'FILIRESTA' as grown in a 17-cm container in a greenhouse in Boskoop, The Netherlands.

Figure 1:
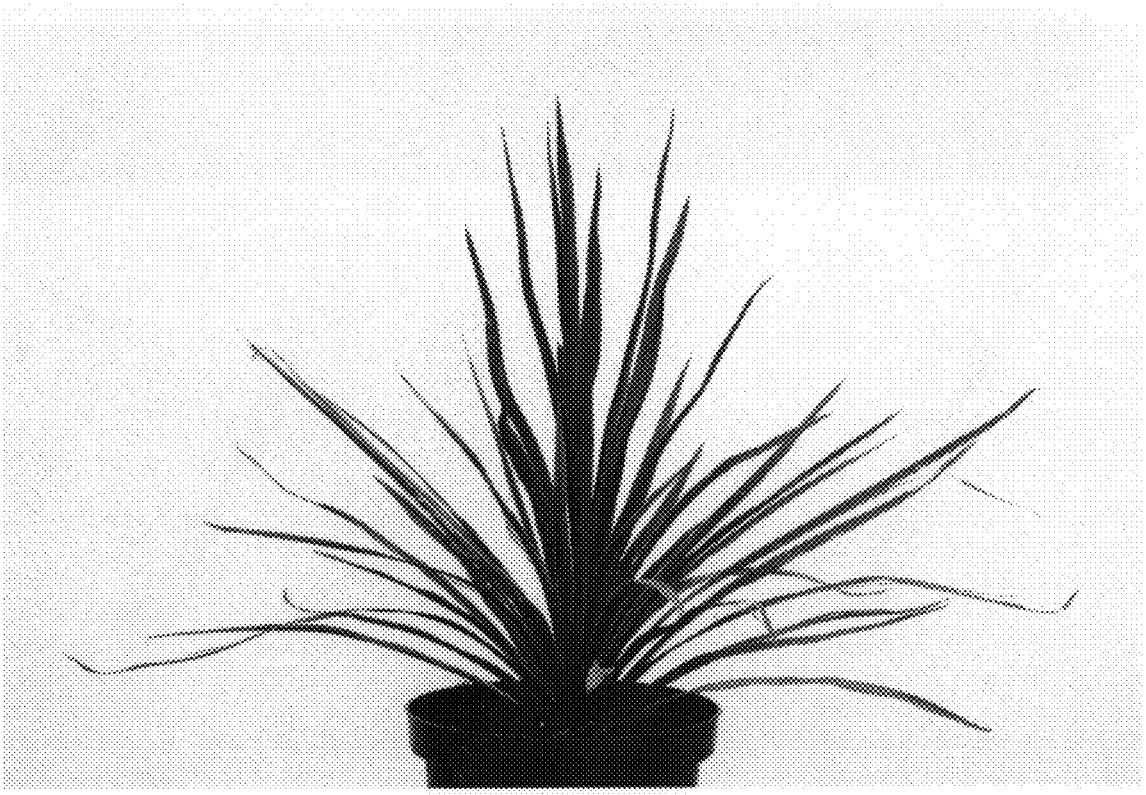

The photograph in FIG. 1 provides a side view of a plant of 'FILIRESTA'.

Figure 2:
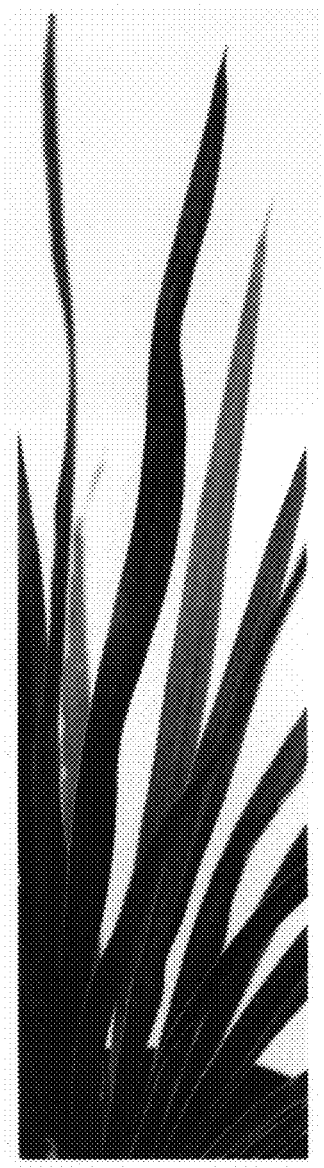

The photograph in FIG. 2 provides a close-up view of the foliage of 'FILIRESTA'.

The colors in the photographs are as close as possible with the photographic and printing technology utilized and color values cited in the detailed botanical description accurately describe the colors of the new *Cordyline*.

DETAILED BOTANICAL DESCRIPTION OF THE PLANT

The following is a detailed description of plants 1.5 years in age as grown in 17-cm containers in a greenhouse in Boskoop, The Netherlands. The phenotype of the new cultivar may vary with variations in environmental, climatic, and cultural conditions, as it has not been tested under all possible environmental conditions. The color determinations are in accordance with The 2015 Colour Chart of The Royal Horticultural Society, London, England, except where general color terms of ordinary dictionary significance are used.

General description:

*Plant type.*—Perennial.

*Plant habit.*—Upright with prodominently cascading foliage.

*Plant size.*—Average of 38.4 cm in height and 58.2 cm in spread as a 1.5-year-old plant, 50 to 60 cm in height and 50 cm in width as a 2-year-old plant.

*Blooming period.*—No flower production has been observed.

*Hardiness.*—At least in U.S.D.A. Zones 9 to 12.

*Diseases and pests.*—No susceptibility or resistance to diseases or pests has been observed.

*Environmental stresses.*—Drought and heat resistant.

*Root description.*—Fibrous.

*Propagation.*—Tissue culture.

*Growth rate.*—Moderate.

*Root development.*—16 weeks to produce a fully rooted young plant for a tissue culture plug.

Stem description: Main shoot grows from base, no stems present.

Foliage description:

*Leaf shape.*—Lorate.

*Leaf division.*—Simple.

*Leaf quantity.*—45.

*Leaf base.*—Sheathing, sheath length; average of 1.9 cm in length, 1.2 cm in width and upper side 155A in color, lower side 155B in color.

*Leaf apex.*—Narrowly acute, slightly tapering at the tip.

*Leaf venation.*—Parallel, upper surface 200B, lower surface 166A.

*Leaf margins.*—Entire, glabrous and smooth.

*Leaf arrangement.*—Alternate in a basal rosette.

*Leaf aspect.*—Held in an average angle of 45° to stem, moderately carinate and slightly arching, tips pointing downward, held at multiple angles.

*Leaf surface.*—Upper surface slightly glossy, lower surface matte.

*Leaf color.*—Young upper surface; N77A, main vein 178B, narrowly margined 180B, young lower surface; 200A, main vein 183A, narrowly margined 178B, mature upper surface a color between N77A and 200A, changing to 165B at the base, narrowly margined 180B, turning to 197A and N199A as the leaves age, mature lower surface; 200A, narrowly margined 178B.

*Leaf size.*—Average of 33.4 cm in length and 1.3 cm in width.

*Petiole.*—None present.

It is claimed:

1. A new and distinct cultivar of *Cordyline* plant named 'FILIRESTA' as herein illustrated and described.

* * * * *